(12) United States Patent
Olig et al.

(10) Patent No.: US 9,827,395 B2
(45) Date of Patent: Nov. 28, 2017

(54) INTERVENTIONAL SINUS ENDOSCOPE

(71) Applicants: Chris P. Olig, Eden Prairie, MN (US); Kester J. Batchelor, Mound, MN (US); Tailin Fan, Nashua, NH (US)

(72) Inventors: Chris P. Olig, Eden Prairie, MN (US); Kester J. Batchelor, Mound, MN (US); Tailin Fan, Nashua, NH (US)

(73) Assignee: Gyrus ACMI, Inc., Southborough, MA (US)

( * ) Notice: Subject to any disclaimer, the term of this patent is extended or adjusted under 35 U.S.C. 154(b) by 214 days.

(21) Appl. No.: 14/155,506

(22) Filed: Jan. 15, 2014

(65) Prior Publication Data
US 2015/0196735 A1    Jul. 16, 2015

(51) Int. Cl.
*A61M 25/00*    (2006.01)
*A61M 25/01*    (2006.01)
*A61B 1/012*    (2006.01)
*A61B 1/233*    (2006.01)
*A61B 1/00*    (2006.01)

(52) U.S. Cl.
CPC ....... *A61M 25/0074* (2013.01); *A61B 1/0014* (2013.01); *A61B 1/012* (2013.01); *A61B 1/233* (2013.01); *A61M 25/0026* (2013.01); *A61M 25/01* (2013.01); *A61B 1/00135* (2013.01); *A61M 2025/0006* (2013.01); *A61M 2025/0025* (2013.01); *A61M 2025/0183* (2013.01)

(58) Field of Classification Search
CPC ... A61B 1/00135; A61B 1/0014; A61B 1/012; A61B 1/233; A61M 2025/0006; A61M 2025/0025; A61M 2025/0183; A61M 25/0026; A61M 25/0074; A61M 25/01
See application file for complete search history.

(56) References Cited

U.S. PATENT DOCUMENTS

| | | |
|---|---|---|
| 6,379,378 B1 | 4/2002 | Werneth et al. |
| 6,524,274 B1 | 2/2003 | Rosenthal et al. |
| 6,905,477 B2 | 6/2005 | McDonnell et al. |
| 7,066,904 B2 | 6/2006 | Rosenthal et al. |
| 7,727,197 B2 | 6/2010 | Secrest et al. |
| 8,025,635 B2 | 9/2011 | Eaton et al. |
| 8,348,890 B2 | 1/2013 | Gerrans et al. |
| 8,414,473 B2 | 4/2013 | Jenkins |

(Continued)

FOREIGN PATENT DOCUMENTS

| | | |
|---|---|---|
| EP | 0818208 B1 | 1/1998 |
| EP | 0818208 A3 | 5/1998 |
| WO | WO 2008/134382 | 11/2008 |

*Primary Examiner* — Imani Hayman
(74) *Attorney, Agent, or Firm* — Gerald P. Kazanjian; Yi Chen (57) ABSTRACT

An apparatus and method are presented for a therapy delivery device including a catheter, an endoscope and an endoscope shaft, one or more attachment features for attaching the catheter to the endoscope, wherein the catheter has an expandable lumen at a distal end and wherein the expandable lumen expands upon injection of a therapy at the proximal end of the catheter. Attachment features may be a series of clips along the length of the catheter for attaching to an endoscope or a second lumen on the catheter wherein an endoscope may through one of said lumens. Targeted therapy delivery may be a hydrogel or a chitosan hydrogel to provide a treatment within a sinus of a patient.

4 Claims, 10 Drawing Sheets

(56) References Cited

U.S. PATENT DOCUMENTS

| | | | |
|---|---|---|---|
| 2005/0049459 A1* | 3/2005 | Hern | A61B 1/00094 600/121 |
| 2006/0235458 A1* | 10/2006 | Belson | A61M 25/0032 606/191 |
| 2007/0142709 A1* | 6/2007 | Martone | A61B 1/00135 600/121 |
| 2008/0195041 A1 | 8/2008 | Goldfarb et al. | |
| 2009/0182273 A1* | 7/2009 | Johnson | A61K 31/00 604/103.02 |
| 2009/0258049 A1 | 10/2009 | Klein et al. | |
| 2009/0312745 A1 | 12/2009 | Goldfarb et al. | |
| 2010/0076269 A1 | 3/2010 | Makower et al. | |
| 2011/0004057 A1 | 1/2011 | Goldfarb et al. | |
| 2011/0004197 A1* | 1/2011 | Sansoucy | A61M 25/0102 604/523 |
| 2011/0150002 A1 | 6/2011 | Kim | |

* cited by examiner

INTERVENTIONAL SINUS ENDOSCOPE

FIELD OF THE INVENTION

The present invention relates to an apparatus and method for inserting a therapy delivery device into a small cavity of a patient, for example a sinus cavity, wherein an expandable section is provided at a distal end of the therapy delivery device for maintaining an expanded state during therapy delivery and an unexpanded state during insertion or removal of the device from the anatomy.

BACKGROUND

Current therapy delivery catheters are typically made to be as small as possible for easy passage into a body tissue or cavity. A therapy may be injected through a catheter lumen and the catheter is then withdrawn from the tissue or body cavity. If the catheter is too large for the passageway, it may cause trauma to the surrounding tissue and make navigation into and through body cavities a challenge. Therefore, it is desirable to have a catheter of a small lumen size which is capable of delivering a therapy without causing trauma to the tissue along the passageway to the desired delivery site.

In the past, instruments for the purpose of injection of a fluid have been used in conjunction with endoscopes. For example, EP0818208A2 describes a working channel of an endoscope being used to pass a catheter and guidewire for this purpose.

Catheters with expandable sections at a distal end are well known in the prior art for the purpose of tissue expansion or dilation as in U.S. Pat. No. 8,414,473B2, and for the purpose of hydrogel delivery as in U.S. Pat. No. 6,524,274, for example. U.S. Pat. No. 6,524,274, however, teaches release of a hydrogel from an outer surface upon contact with a triggering agent, rather than hydrogel delivery through a catheter as in the present invention.

Despite the approaches discussed above, there is still a need for a catheter conduit with a diameter large enough for injection of a viscous hydrogel fluid into an anatomical region of interest, for example into a sinus cavity.

In addition, there is a need for such a conduit to be provided with an expandable section at a distal end such that a thicker, more viscous fluid is able to elute through various pores or holes in an outer surface of the expandable section to provide a more even distribution of a therapy to the surrounding anatomical structures.

There is also a need for such a catheter conduit to be insertable into an anatomical region of interest provided along a path consistent with the shaft of an endoscope such that visualization of the anatomical space for therapy delivery is possible. In sinus procedures, for example, this path would be a non-straight line path for targeted delivery into a sinus cavity.

SUMMARY OF THE INVENTION

The present invention meets one or more of the above needs by providing an interventional sinus endoscope which has the ability to change between an unexpanded state to an expanded state for the purposes of providing a therapy. The interventional sinus endoscope may consist of a catheter with attachment features for attaching to an outer surface of a shaft of an endoscope, provided with an expandable section at a distal end of the catheter for expansion during injection of a therapy which is capable of returning to a non-expanded state during insertion or removal of the device to or from an anatomical area of interest.

Therapy delivery through the expandable catheter may be delivery of a viscous material, such as a gel, hydrogel or a chitosan based hydrogel, and may also be another type of fluid, including liquid, dyes, or contrast agents. Hydrogels consist of a cross-linked macromolecular network that swell in water or in biological fluids. They may function as carriers or bioactive macromolecules which may be used for stopping bleeding, as a wound dressing, or for the slow release of drugs to encourage healing following a surgical procedure. Contrast agents or dyes may be used to check the patency of the fallopian tubes, for example.

Target anatomy areas for use of the present invention include the sinuses, however the device could be used for targeted delivery of viscous material into other anatomical regions, including but not limited to the urethra, the gastrointestinal tract, or other anatomical locations fir which an endoscope provided with a therapy delivery device may be desired to be used.

In one exemplary embodiment, the expandable section is provided with pores or holes along a top surface to allow for an even distribution of hydrogel therapy to an anatomical region of interest once the device is fully inserted. The expandable distal end section of the catheter may be provided with an elastic modulus that would encourage retraction to an unexpanded state after delivery of the hydrogel therapy is complete within a reasonable timeframe to accommodate a surgical procedure or an outpatient procedure in a doctor's office.

Accordingly, pursuant to one aspect of the present invention, there is contemplated an apparatus comprising: a therapy delivery device, comprising a catheter with a proximal end and a distal end; an endoscope with a proximal end and a distal end and an endoscope shaft with a proximal end and a distal end; one or more attachment features are provided for attaching a distal portion of the catheter to a distal portion of the endoscope such that the endoscope may be slidably received within the catheter; the catheter has an expandable lumen at a distal end; and the expandable lumen expands upon injection of a therapy at the proximal end of the catheter.

The invention may be further characterized by one or any combination of the features described herein, such as: the one or more attachment features consist of a series of clips along a length of the catheter that attaches to at least a portion of a circumference of an outside surface of the endoscope shaft; the expandable lumen only expands away from the endoscope shaft; the expandable lumen is porous to allow for release of the therapy through an outer surface of the expandable lumen; the therapy is deliverable through a distal tip of the catheter; the therapy is deliverable through both a distal tip and the outer surface of the expandable lumen of the catheter; or the therapy is deliverable through the outer surface of the expandable lumen of the catheter.

Pursuant to yet another aspect of the present invention, there is contemplated an apparatus, comprising a therapy delivery device comprising a bilumen catheter comprising a first lumen and a second lumen, an endoscope and an endoscope shaft, a distal end of the endoscope shaft is insertable through said second lumen of the bilumen catheter, and the first lumen of the bilumen catheter is an expandible lumen at a distal end.

The invention may be further characterized by one or any combination of the features described herein, such as: the therapy is a hydrogel, or the therapy is a chitosan hydrogel.

Pursuant to yet another aspect of the present invention, there is contemplated a method for delivering a therapy, comprising placing a catheter adjacent to an endoscope shaft; the catheter is provided with one or more attachment features in order to slidably engage the endoscope shaft; inserting the catheter and the endoscope shaft into a sinus passage; injecting a therapy at a proximal end of the catheter and thereby forcing an expandable section at a distal end of the catheter to expand to cause elution of the therapy into the surrounding anatomy; and the expandable section would collapse after therapy delivery for easy removal through the sinus passage.

The invention may be further characterized by one or any combination of the features described herein, such as: the one or more attachment features is a series of clips along a length of the catheter that attaches to at least a portion of a circumference of an outside surface of the endoscope shaft; or the one or more attachment features is a second lumen of the catheter, provided along the length of the catheter and large enough to fit endoscope shaft therethrough.

Further aspects, advantages and areas of applicability will become apparent from the description provided herein. It should be understood that the description and specific examples are intended for purposes of illustration only and are not intended to limit the scope of the present disclosure.

DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

As will be seen, the devices and methods taught herein offer improved targeted therapy treatment of an anatomical region which might otherwise be difficult to access with an endoscope provided with delivery system for the delivery of a viscous material.

The present invention describes an interventional sinus endoscope or therapy delivery device which is provided with an improved expandable catheter system. The expandable catheter system may be provided with one or more attachment features for connecting to an endoscope such that visualization of the anatomy of interest would be possible to identify the target anatomy of interest before proceeding with injection of a therapy.

It is contemplated that a catheter is provided with one or more attachment features in such a way that it may be made attachable to an endoscope along the length of the endoscope. In one embodiment, a catheter may be provided with a section along the circumference which is a rigid spine which makes contact with a surface of an endoscope. The rigid spine may be a thin section, with a thickness in the range of about 0.127 mm to about 1.016 mm, preferably in the range of about 0.178 mm to about 0.762 mm, and most preferably in the range of about 0.254 mm to about 0.508 mm. The diameter of the endoscope may typically be in the range of approximately 3 mm+/−0.01 mm.

In one embodiment, a series of flexible prongs, clips, rings or the like may be provided along the length of the catheter, or alternatively an adhesive may be provided, which is connected into the rigid spine portion, to provide attachment for the expandable lumen of the catheter along the length of the endoscope shaft and thereby resist a sliding motion from occurring between the catheter and endoscope. In an alternate embodiment, the catheter is a bitumen catheter comprising a first lumen and a second lumen. The first lumen may be an expandable lumen for the delivery of a therapy and the second lumen may be used for insertion of the endoscope shaft. The endoscope may be inserted at a proximal end of the bitumen catheter and slid through such that the distal tip of the endoscope mates with the distal tip of the second lumen of the bilumen catheter.

It is contemplated that if the endoscope is a straight shaft rigid endoscope, the one or more attachment features would allow the catheter to matingly engage with the shaft of the endoscope along the length of the endoscope such that upon insertion and removal of the therapy delivery device the endoscope and catheter would remain matingly engaged.

Alternatively, if the endoscope was a sinus endoscope, for example, such that the distal end of the endoscope was oriented in a non-straight path from the proximal end of the endoscope, the one or more attachment features provided on the expandable catheter system of the therapy delivery device may allow for the catheter to match the non-straight path of the endoscope by following the angle from the proximal end to the distal end.

This rigid spine section may be in direct contact with the surface of the endoscope. The rigid spine may matingly engage with the endoscope shaft and may make contact with the endoscope surface along a portion of its circumference. The rigid spine may be such that it lies on top of the endoscope and covers an upper portion of the outer circumference of the endoscope surface, in the range of about 60-100 degrees of the circumference of the endoscope surface, preferably in the range of about 70-90 degrees along the length of the circumference of the endoscope surface, or more preferably in the range of about 60-80 degrees along the length of the circumference of the endoscope surface. The rigid spine may be composed of a polymer, more particularly a nylon support material.

The remainder of the circumference of the catheter may be composed of a balloon wall that expands upon injection of a therapy. The desired length of the expandable portion is dependent on the anatomy being traversed by the catheter. In one embodiment, the entire length of the catheter portion which is attached to the endoscope is capable of expanding upon injection of a therapy. In alternate embodiments, only a distal portion of the balloon expands upon injection of a therapy. It is contemplated that in anatomical regions where a size limitation exists such as in the nasal passages, i.e. in the vicinity of a 1 mm ostia, the embodiment where only a distal portion of the balloon is expandable may be the best mode of operation.

The expandable wall may be a soft, compliant material that minimizes tissue trauma during expansion and that would deflate or collapse in a timeframe such that it would be reasonable to use in a surgical procedure or in an outpatient office procedure.

Non-compliant polymers may be used for the region of the catheter which is not intended to expand, such as PET or Nylon by way of example. Compliance ranges for non-compliant polymers are typically in the range of 0-10%. Compliant polymers may be used for the region of the catheter which is intended to expand, such as polyurethane, nylon elastomers, or other thermoelastic elastomers, by way of example. Compliance ranges for compliant polymers are typically in the range of 20-100% or more. It is contemplated that semi-compliant polymers may also be used in sections of the expandable catheter. Semi-compliant polymers may be PET, nylon, polyurethane, or other thermoelastic elastomers, which may have compliance ranges from about 10-20%.

In one embodiment, the catheter may be connected at a proximal end to a syringe. The syringe may be used to inject a therapy, which may include a gel, a hydrogel, a fluid, including a liquid, a dye or a contrast agent, into the expandable catheter. The syringe may be a standard syringe or a bulb syringe of a size conducive to the transport of a therapy of interest. The syringe may be connected with a luer lock connector to the tubing of the expandable catheter.

Targeted therapy delivery may be injection of a solution, a gel, a hydrogel, or a liquid that delivers a medication for the treatment or prevention of a disease state, for example for the prevention of infective rhinitis following a surgical procedure. The targeted therapy may be a compound with an anti-inflammatory carbohydrate polymer with a steroid. The anti-inflammatory carbohydrate polymer may be chitosan. Chitosan is an inert substance which may reduce inflammation and which encourages hemostasis and aids in healing.

In one embodiment of the invention, a chitosan hydrogel is used for the purposes of wound healing and may be formed by crosslinking chitosan with a crosslinking agent, such as glutaraldehyde, formaldehyde, epoxy compounds, dialdehyde or starch for example. Chitosan is a linear polysaccharide composed of randomly distributed deacetalylated units (β-(1-4)-linked D-glucosamine) and acetylated units (N-acetyl-D-glucosamine) that is formed from crustacean shells using sodium hydroxide.

Figure 1:
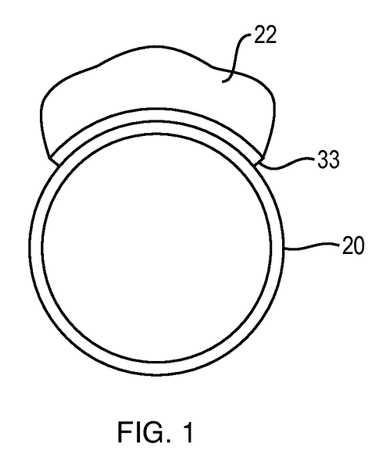
FIG. 1 is a cross-sectional view of the expandable catheter in an unexpanded state attached to an outer surface of an endoscope.

Turning now to the drawings to illustrate examples of embodiments of the present teachings, FIG. 1 details a cross section of a distal end of one embodiment of the device of the present invention, an expandable catheter in an unexpanded state (collapsed catheter) 22 attached with a rigid spine 33 to an outer surface of an endoscope 20. It is contemplated that rigid spine 33 may be a thin polymer or nylon in the range of about 0.229 mm to about 0.356 mm, preferably in the range about 0.254 mm to about 0.330 mm, and more preferably in the range of about 0.279 mm to about 0.305 mm. The diameter of the distal end of endoscope 20 may be typically approximately 3 mm+/−0.01 mm.

Figure 2:
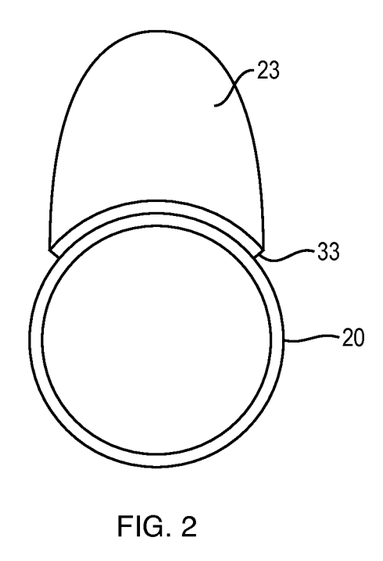
FIG. 2 is a cross-sectional view of the expandable catheter in an expanded state attached to an outer surface of an endoscope.

FIG. 2 details a cross section of a distal end of the device of the present invention, showing the endoscope 20, rigid spine 33 and expanded catheter 23. The device may typically be inserted in the anatomy of interest in the configuration in FIG. 1 and once the target anatomy region was reached, a therapy may be infused into the proximal end of the device causing expansion of the expandable catheter as in FIG. 2 and delivered to the region of interest.

Figure 3:
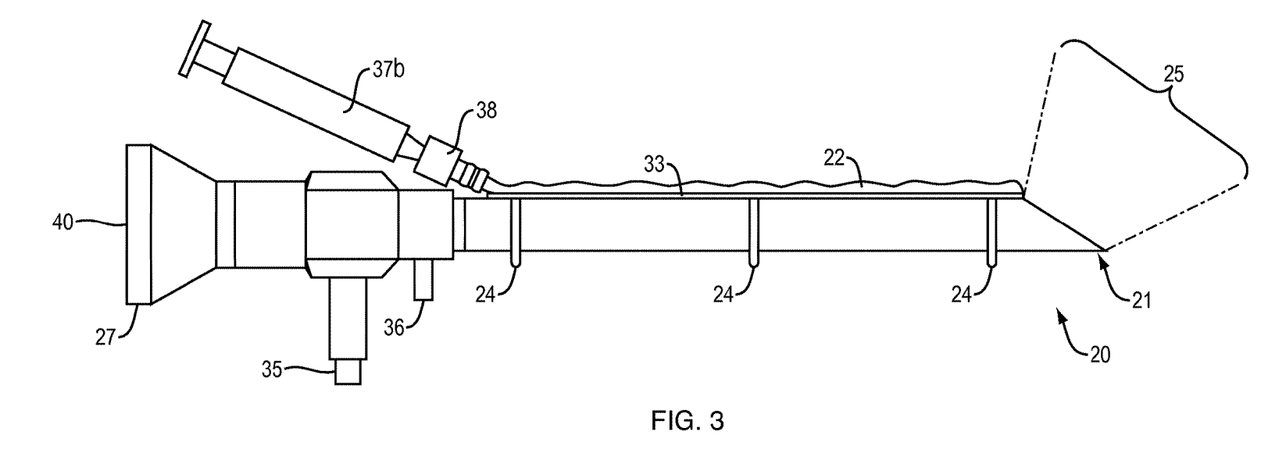
FIG. 3 is a longitudinal side view of the expandable catheter in an unexpanded state attached using attachment features to an outer surface of an endoscope.
Figure 4:
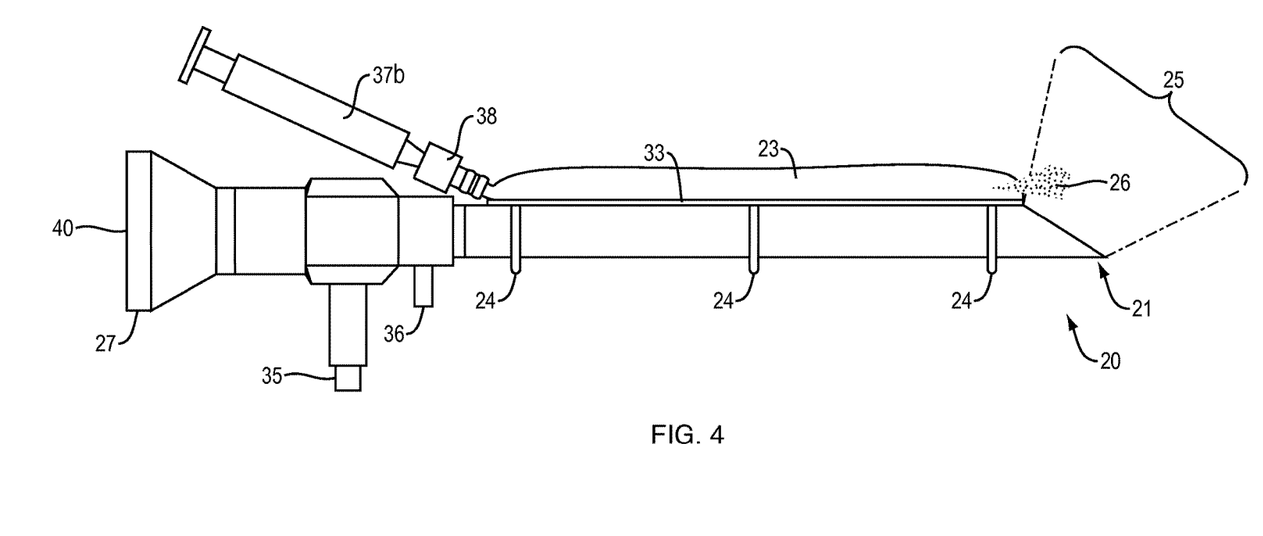
FIG. 4 is a longitudinal side view of the expandable catheter in an expanded state, wherein a majority of the length of the expandable catheter expands during injection of a therapy, attached using attachment features to an outer surface of an endoscope.

FIGS. 3 and 4 detail a longitudinal side view of one embodiment of the device as a whole. Attachment features 24 extend from rigid spine 33 to surround endoscope 20 and matingly engage collapsed catheter 22 during insertion of the device into the anatomical region of interest. Once the endoscope has reached the desired anatomical region of interest, a therapy 26 is injected and the compliant material forming collapsed catheter 22 expands into expanded catheter 23 as the therapy or hydrogel 26 is infused into the anatomical region of interest. Field of view (FOV) 25 illustrates the viewing area in front of endoscope distal end 21. Syringe 37b connects via luer lock connector 38 into collapsed catheter 22. At the proximal end 27 of the device, endoscope ocular 40 allows a user to view the anatomical region of interest. Light post 35 allows for connection to a light source to provide illumination at the endoscope distal end via fiber optic cables. Suction port 36 connects with a suction channel within endoscope 20 and provides for suction capability at the endoscope distal end 21.

It is contemplated that the device of the present invention may work with endoscopes of different shapes and sizes and which are designed for different fields of view. For example, endoscopes which are more desirable for use in the nose may have non-straight tips. Attachment features 24 are intended to provide attachment to endoscopes of any shape and size and still deliver therapy 26 to a target anatomical region of interest, i.e. at the tip of the endoscope.

Figure 5:
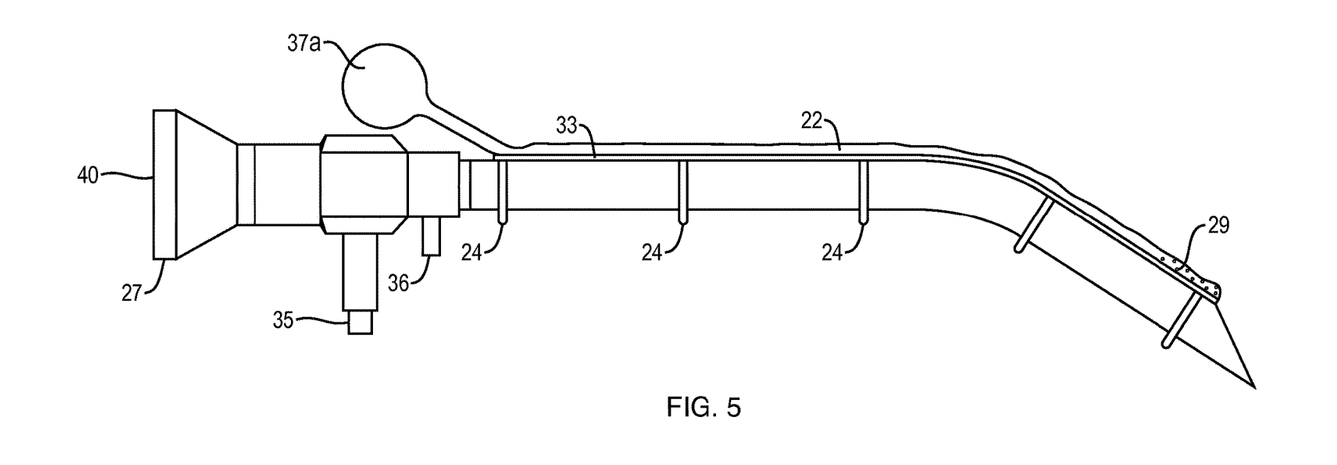
FIG. 5 is a longitudinal side view of the expandable catheter in an unexpanded state attached using attachment features to an outer surface of an endoscope.
Figure 6:
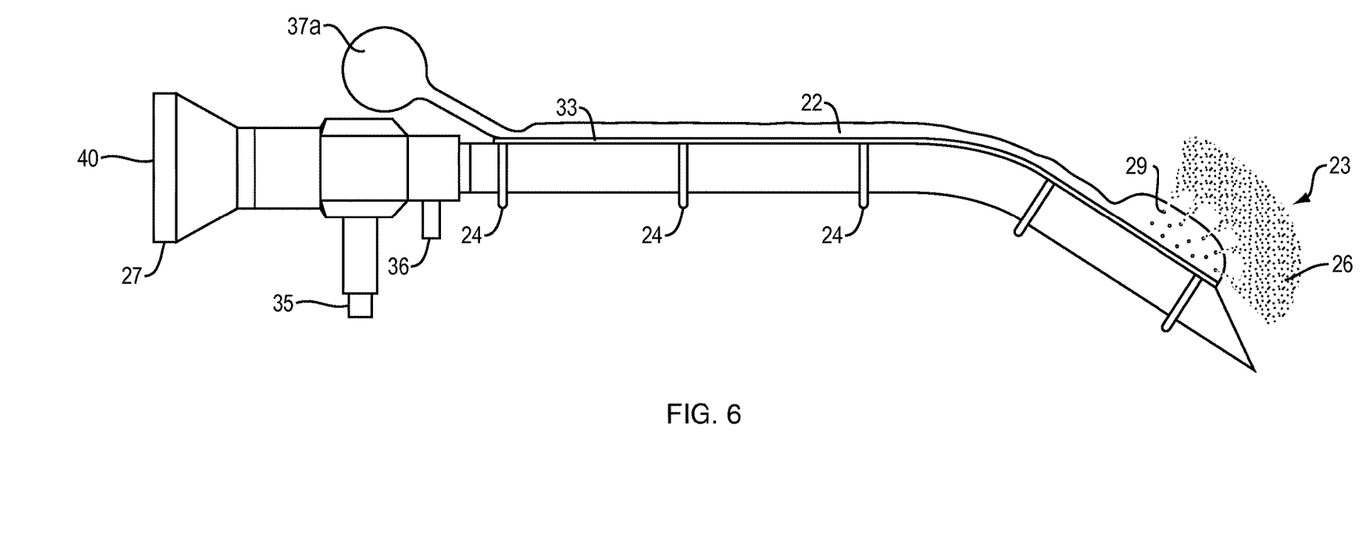
FIG. 6 is a longitudinal side view of the expandable catheter in an expanded state, wherein a section at the distal tip of the expandable catheter expands during injection of a therapy, attached using attachment features to an outer surface of an endoscope.

FIGS. 5 and 6 detail an alternate embodiment of the present invention wherein the endoscope attachment features 24 which connect to rigid spine 33 aid in maintaining contact of the expandable catheter with the endoscope 20 along its length, including along the non-straight distal tip. Catheter 22 is provided with pores or holes 29 at the distal end such that upon infusion of a therapy 26 into the expandable catheter, the therapy 26 may be delivered both through a hole at the distal most end of expanded catheter 23 as well as through several additional pores or holes 29 which may provide for more generalized coverage of the therapy 26 to the anatomical region of interest. FIGS. 5 and 6 show use of a bulb syringe 37a connected to a proximal end of collapsed catheter 22. At the proximal end 27 of the device, endoscope ocular 40 allows a user to view the anatomical region of interest. Light post 35 allows for connection to a light source to provide illumination at the endoscope distal end via fiber optic cables. Suction port 36 connects with a suction channel within endoscope 20 and provides for suction capability at the endoscope distal end 21.

Figure 7A:
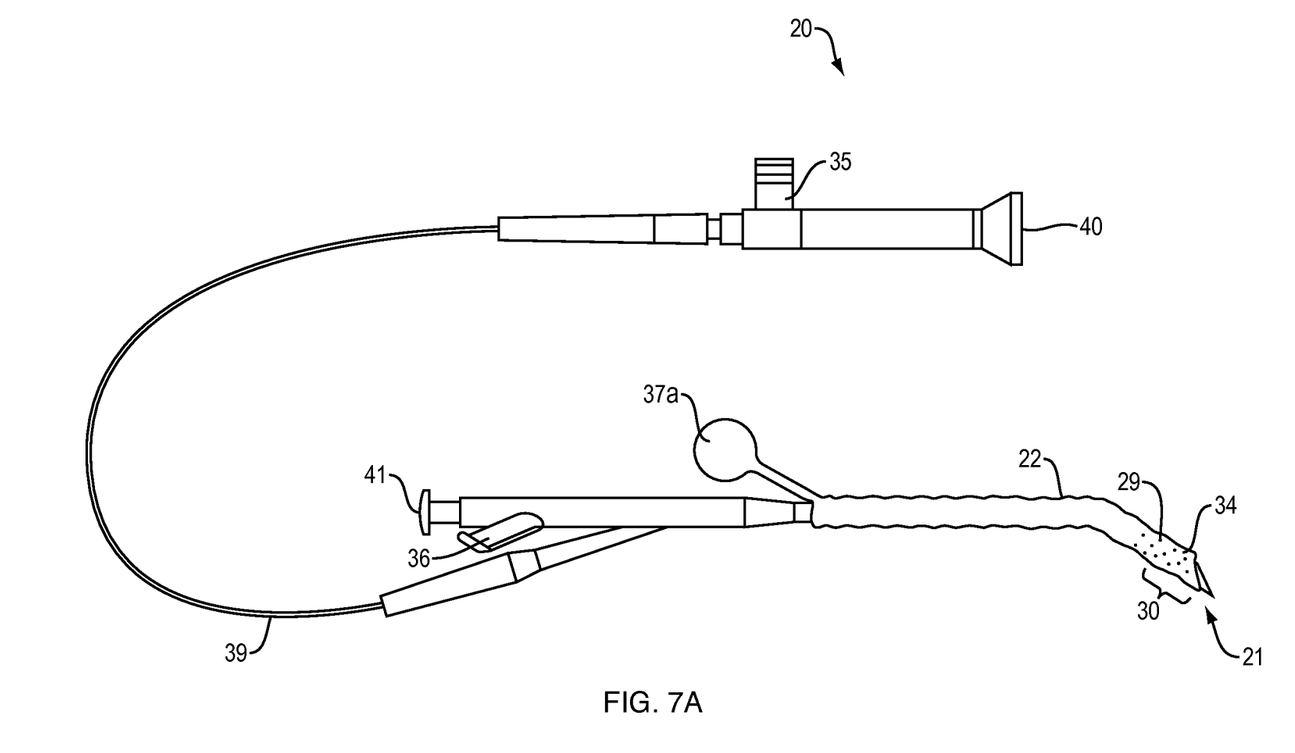
FIG. 7A is a longitudinal side view of the expandable catheter in one embodiment attached to a sinus endoscope, in an unexpanded state.
Figure 7B:
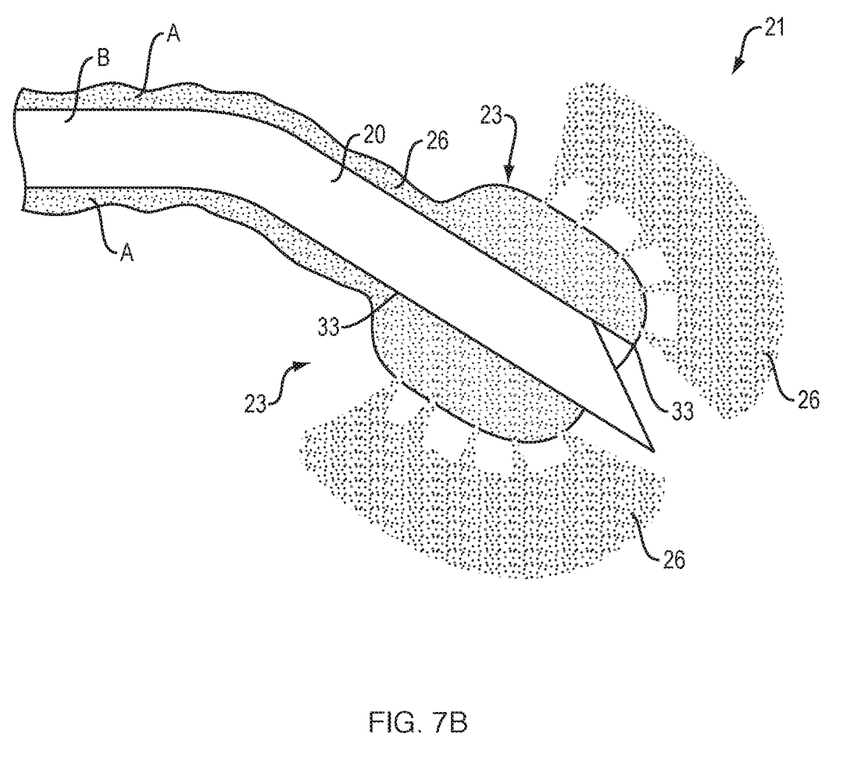
FIG. 7B is an expanded view of the device tip of the embodiment of FIG. 7A of the expandable catheter in the expanded state during infusion of a therapy.
Figure 7C:
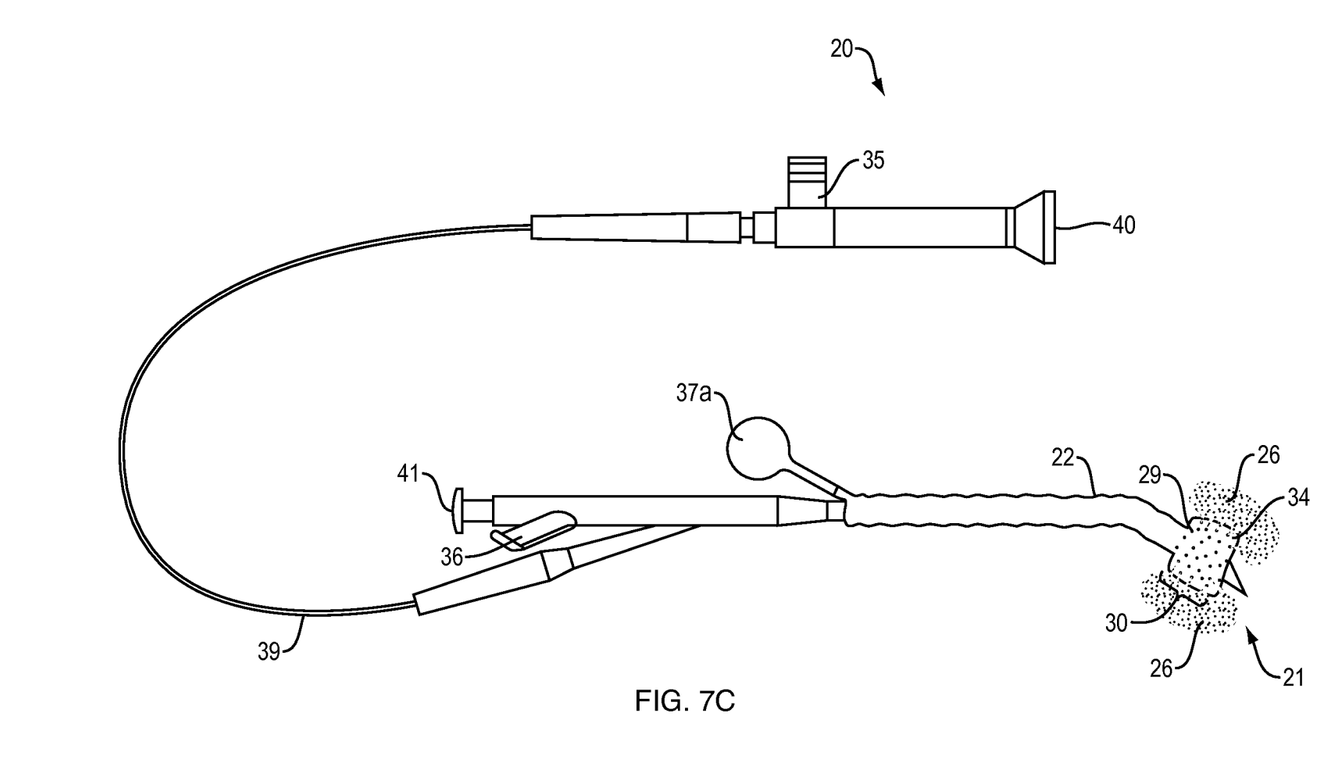
FIG. 7C is a longitudinal side view of the expandable catheter in the embodiment shown in FIG. 7A attached to a sinus endoscope, in the expanded state.

FIGS. 7A-C detail an alternate embodiment of the present invention wherein a multi-lumen catheter 34 surrounds a sinus endoscope 20. A main central lumen is slid over endoscope 20 such that the endoscope distal end 21 protrudes just past the distal end of the expandable catheter to enable visibility of the anatomical region of interest. An outer lumen surrounds the main lumen and is expandable upon injection of a therapy 26. Holes or pores 29 may be provided at the distal end of catheter 22 about the entire outer circumference at a distal end region at the angled tip 30 of sinus endoscope 20 such that upon infusion of a therapy 26 into the expandable catheter, the therapy 26 may be delivered both through a hole at the distal most end of expanded catheter 23 as well as through several additional pores or holes 29 which may provide for more generalized coverage of the therapy 26 to the anatomical region of interest. FIGS. 7A and 7C illustrate use of a bulb syringe 37a connected to a proximal end of catheter 22. Endoscope ocular 40 allows a user to view the anatomical region of interest. Light post 35 allows for connection to a light source to provide illumination at the endoscope distal end via fiber optic cables 39. Suction port 36 connects with a suction channel within endoscope 20 and provides for suction capability at the endoscope distal end 21. Working channel 41 allows for the introduction of additional surgical tools into the anatomical region of interest to accomplish tasks such as tissue resection, for example. FIG. 7B details a hydrogel or therapy 26 being infused through catheter 23 to regions both above and below endoscope 20.

Figure 8A:
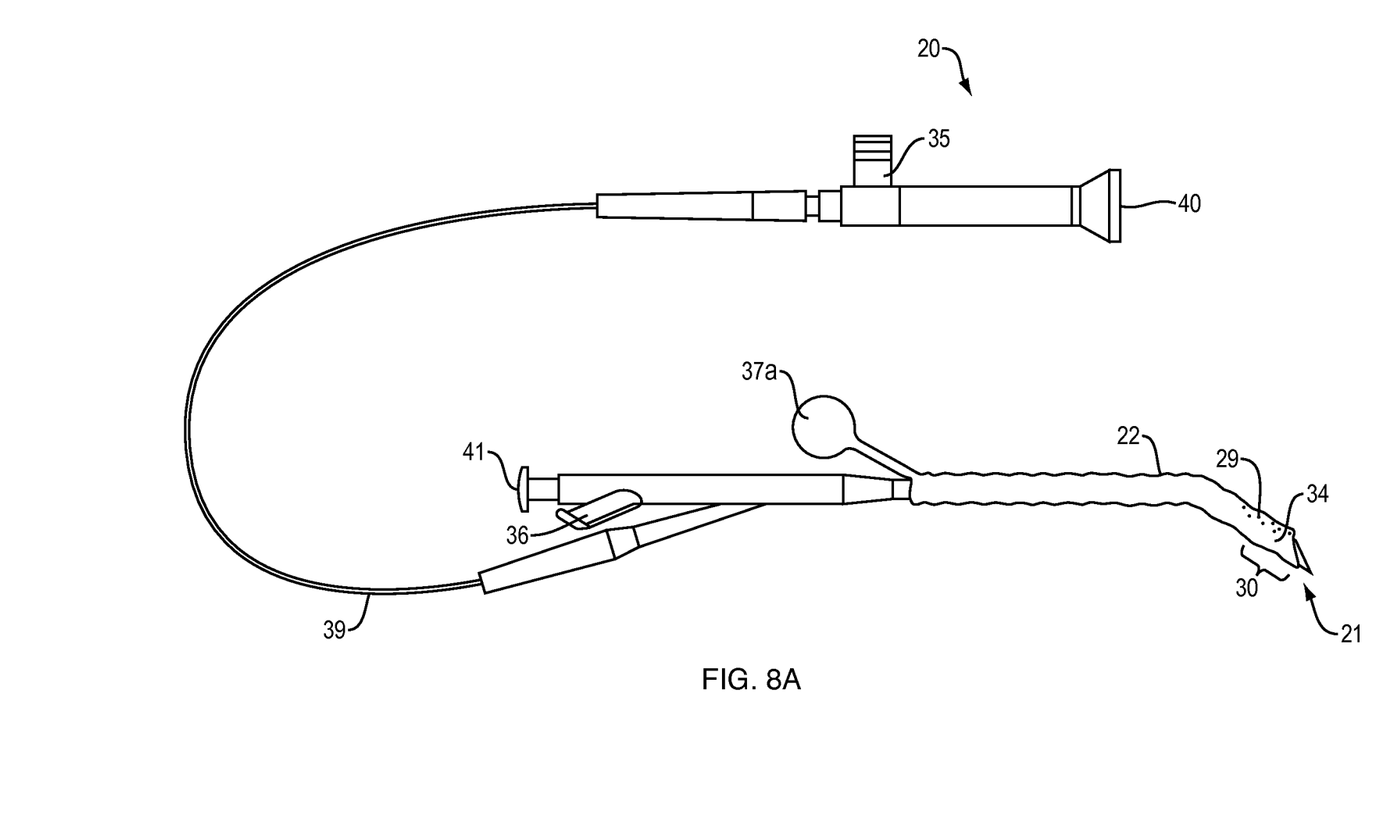
FIG. 8A is a longitudinal side view of the expandable catheter in one embodiment attached to a sinus endoscope, in an unexpanded state.
Figure 8B:
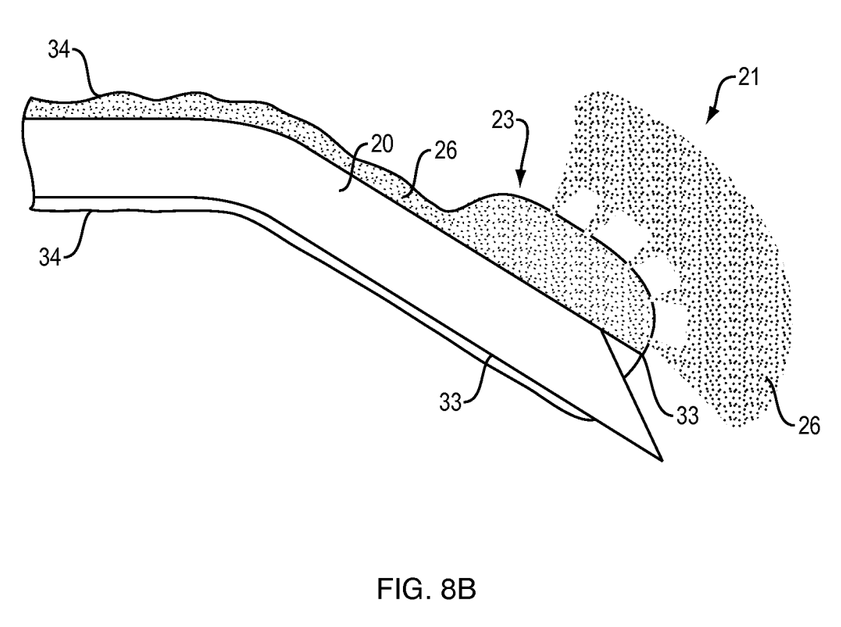
FIG. 8B is an expanded view of the device tip from the embodiment shown in FIG. 8A of the expandable catheter in the expanded state during infusion of a therapy.
Figure 8C:
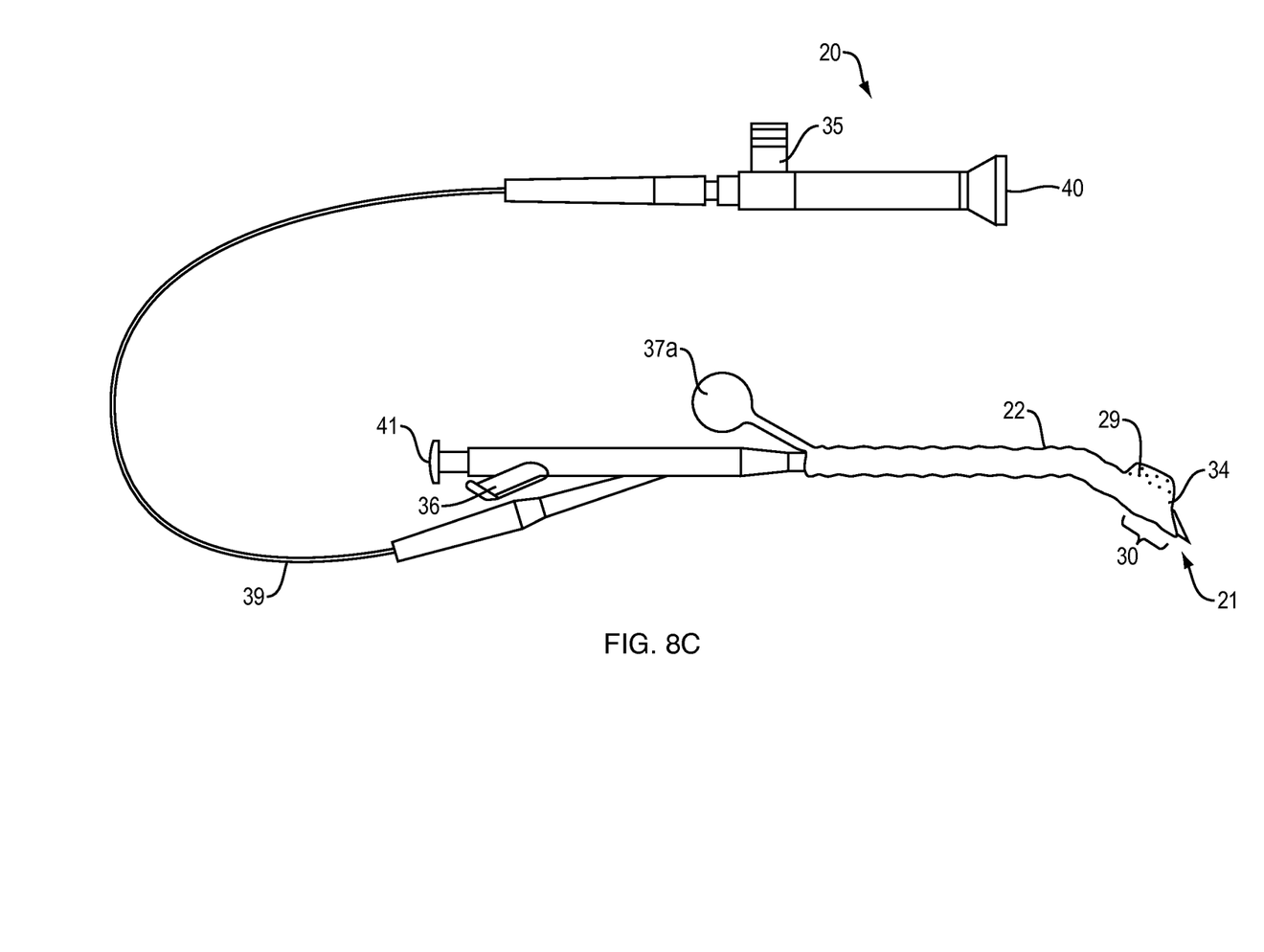
FIG. 8C is a longitudinal side view of the expandable catheter in the embodiment shown in FIG. 8A attached to a sinus endoscope, in the expanded state.

FIGS. 8A-C detail an alternate embodiment of the present invention wherein a bitumen catheter 34 surrounds endoscope 20. A main lumen is slid over endoscope 20 such that the endoscope distal end 21 protrudes just past the distal end of the expandable catheter to enable visibility of the anatomical region of interest. An additional lumen is provided alongside the main lumen and is expandable upon injection of a therapy 26. Rigid spine 33 is provided on the inside portion of the main lumen of catheter 22 to provide stability as the endoscope slides through. Holes or pores 29 may be provided at the distal end of catheter 22 along the outer circumference of the additional lumen about an upper portion at a distal end region such that upon infusion of a therapy 26 into the expandable catheter 22, the therapy 26 may be delivered both through a hole at the distal most end of expanded catheter 23 as well as through several additional pores or holes 29 which may provide for more generalized coverage of the therapy 26 to the anatomical region of interest. FIGS. 8A and 8C illustrate use of a bulb syringe 37a connected to a proximal end of catheter 22. Endoscope ocular 40 allows a user to view the anatomical region of interest. Light post 35 allows for connection to a light source to provide illumination at the endoscope distal end via fiber optic cables 39. Suction port 36 connects with a suction channel within endoscope 20 and provides for suction capability at the endoscope distal end 21. Working channel 41 allows for the introduction of additional surgical tools into the anatomical region of interest to accomplish tasks such as tissue resection, for example. FIG. 8B details a hydrogel or therapy 26 being infused through catheter 23 to a region above endoscope 20.

Figure 9:
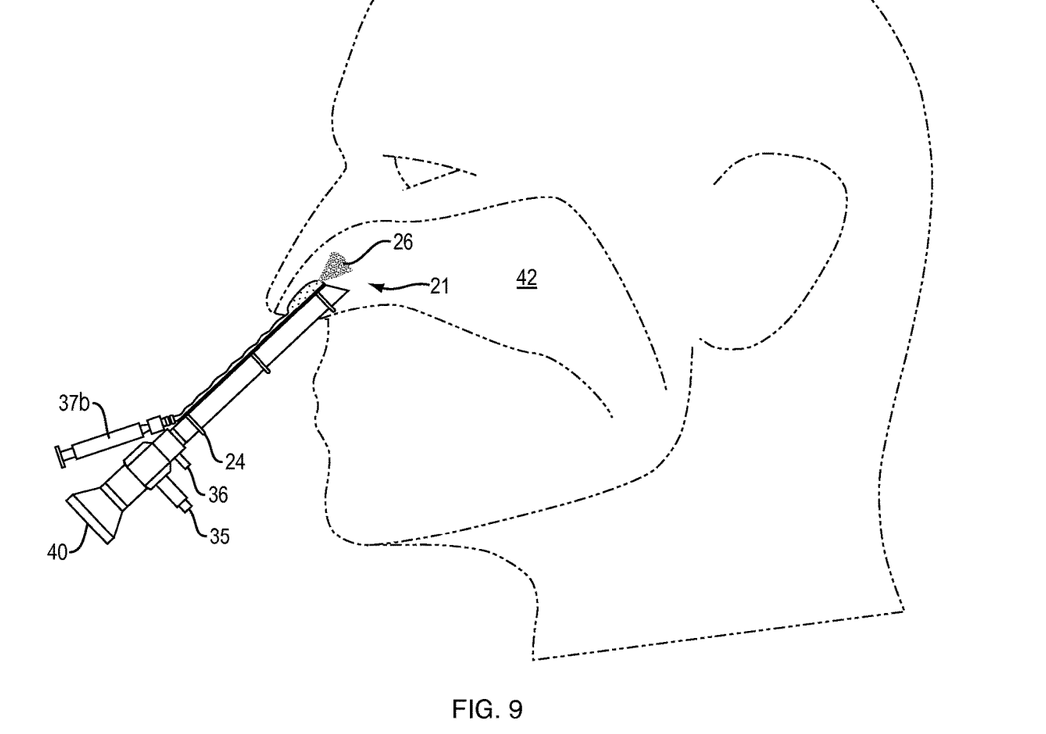
FIG. 9 shows anatomical placement of a longitudinal side view of one embodiment of the invention.

FIG. 9 details one embodiment of present invention being used in the sinuses 42 of a patient.

It is contemplated embodiments or examples described above may not be mutually exclusive and may be used in combination with each other.

Unless stated otherwise, dimensions and geometries of various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

Preferred embodiments of the present invention have been disclosed. A person of ordinary skill in the art would realize, however, that certain modifications would come with the teachings of the invention. Therefore, the following claims should be studied to determine the true scope and content of the invention.

Any numerical values recited in the above application include all values from the lower value to the upper value in increments of one unit provided that there is a separation of at least two units between any lower value and any higher value. As an example if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01, or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" and "approximately" in connection with a range applies to both ends of the range. Thus, "about 20 to about 30" is intended to cover "about 20 to about 30." Inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements, ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

Plural elements, ingredients, components or steps can be provided by a single integrated element, ingredient, component or step might be divided into separate plural elements, ingredients, components or steps. The disclosure of "a" or "one" to describe an element, inbredient, component or step is not intended to foreclose additional elements, ingredients, components, or steps.

20 Endoscope
21 Endoscope distal end
22 Collapsed catheter/Catheter
23 Expanded catheter
24 Attachment features
25 FOV
26 Therapy, including a gel, hydrogel or a chitosan based hydrogel, and may also be another type of fluid, including liquid, dyes, or contrast agents
27 Endoscope proximal end
29 Holes or pores in distal region of expandable catheter
30 Angled tip of sinus endoscope
32 Straight shaft endoscope
33 Rigid Spine
34 Multi-lumen catheter
35 Light post
36 Suction port
37a Bulb Syringe
37b Syringe
38 Luer lock connector
39 Fiber optic cable
40 Endoscope ocular
41 Working channel
42 Sinus

The invention claimed is:

1. An apparatus, comprising: a therapy delivery device, comprising:
a multi-lumen catheter comprising at least a first lumen and a second lumen, the first lumen surrounding the second lumen; and
an endoscope and an endoscope shaft,
wherein a distal end of the endoscope shaft is insertable through said second lumen of the multi-lumen catheter,
wherein the first lumen of the multi-lumen catheter is an expandable lumen at a distal end, and
wherein the distal end of the first lumen comprises a plurality of pores along a top surface, and selectively expands upon injection of a therapy such that the distal end of the first lumen expands more than a section of the first lumen extending towards the distal end of the first lumen,
wherein the section of the first lumen comprises a non-compliant polymer having a compliance range of 0-10%, and the distal end of the first lumen comprises a compliant polymer having a compliance range of 20-100%.

2. The apparatus of claim 1, wherein the therapy includes at least one of a gel, a hydrogel, a fluid, a liquid, a dye and a contrast agent.

3. The apparatus of claim 2, wherein the therapy is a chitosan based hydrogel.

4. The apparatus of claim 1, wherein the multi-lumen is a bilumen.

* * * * *